US006402699B1

(12) United States Patent
Kodama et al.

(10) Patent No.: US 6,402,699 B1
(45) Date of Patent: Jun. 11, 2002

(54) METHOD OF MAKING A DECISION ON THE MONTHLY PHYSIOLOGICAL CONDITION OF A FEMALE BODY, APPARATUS WHICH MAKES SUCH DECISION, AND APPARATUS WHICH PRODUCES SOME DATA FOR SUCH DECISION

(75) Inventors: Miyuki Kodama; Hitoshi Sato, both of Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/657,100

(22) Filed: Sep. 7, 2000

(30) Foreign Application Priority Data

Sep. 13, 1999 (JP) .......................................... 11-258538

(51) Int. Cl.[7] ................................................ A61B 5/00
(52) U.S. Cl. ..................................................... 600/551
(58) Field of Search ................................ 600/547, 551, 600/591

(56) References Cited

U.S. PATENT DOCUMENTS 4,784,155 A 11/1988 Mills
5,499,631 A 3/1996 Weiland

FOREIGN PATENT DOCUMENTS

EP 0 339 092 A1 11/1989
EP 0 344 770 A1 12/1989
EP 0 498 303 A1 8/1992

*Primary Examiner*—Max Hindenburg
(74) *Attorney, Agent, or Firm*—McDermott, Will & Emery (57) ABSTRACT

The invention relates to a method of making a decision on the monthly physiological condition of a female body, such as ovulation and PMS, an apparatus which makes such decision, and an apparatus which produces some data for such decision. To enable such decision to be made, the bioelectric impedance of the female body is determined periodically to provide a historical record of bioelectric impedance representing how it has been varying; and a required decision is made by comparing the present bioelectric impedance with the historical record of bioelectric impedance or the historical record of bioelectric impedance is displayed, representing how it has been varying.

28 Claims, 12 Drawing Sheets

SUBJECT A: CORRELATION BETWEEN WEIGHT AND BI APPEARING BETWEEN BOTH FEET (NO MODIFICATION)

R: CORRELATION COEFFICIENT
IT REPRESENTS THE DEGREE TO WHICH TWO VARIABLES CORRELATE.
IT CAN REPRESENT ANY NUMBER FROM 0.0 TO 1.0. THE HIGHER THE VALUE IS, THE STRONGER THE CORRELATION IS. (R=0.0 MEANS THERE IS NO CORRELATION, AND R=1.0 INDICATES A STRAIGHT LINE OF X=Y.)

SUBJECT A: CORRELATION BETWEEN BASAL BODY TEMPERATURE AND WEIGHT-MODIFIED BI APPEARING BETWEEN BOTH FEET

R: CORRELATION COEFFICIENT

METHOD OF MAKING A DECISION ON THE MONTHLY PHYSIOLOGICAL CONDITION OF A FEMALE BODY, APPARATUS WHICH MAKES SUCH DECISION, AND APPARATUS WHICH PRODUCES SOME DATA FOR SUCH DECISION

FIELD OF THE INVENTION

The present invention relates to a method of making a decision on the monthly physiological condition of a female body, such as ovulation, PMS (premenstrual syndrome), menstruation, fertilizable condition or other female physical conditions which appear in a monthly cycle. Also, it relates to an apparatus which makes a decision on the monthly physiological condition of a female body, and an apparatus which produces some useful data in making such a decision.

PRIOR ART

Figure 1:
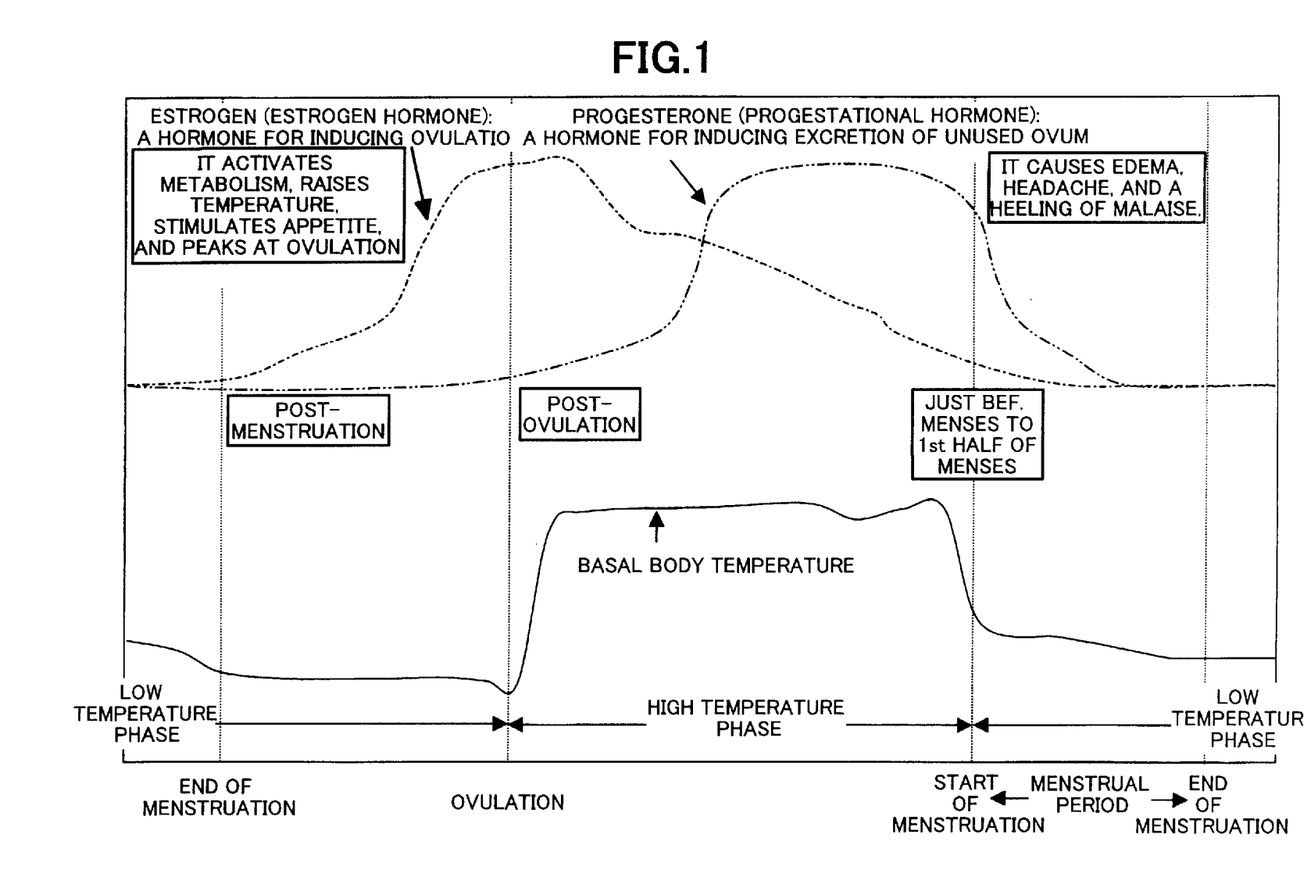
FIG. 1 illustrates how basal body temperature, secretion of hormones (ordinate) and the monthly physiological condition of a female body vary with time (abscissa)

As seen from FIG. 1, the monthly physiological condition of a female body is closely related with the basal body temperature as for instance follows: the basal body temperature transfers from the low temperature phase to the high temperature phase on the day of ovulation, and from the high temperature phase to the low temperature phase on the menstruation start day. Women, therefore, measure their basal body temperature with a gynecological thermometer for the purpose when they wake up every morning, so that a record of basal body temperature may be prepared for making a required decision on their physiological conditions.
Problems to be solved by the invention:

It, however, takes about five or more minutes to measure their basal body temperature while they lay in bed every day without moving. This is bothersome more or less, and they are apt to fall a sleep before without knowing it, sometimes even oversleeping.

Also, the record of basal body temperature makes it possible as described above to determine only some of physiological condition of a female body, which are usually used for birth control, such as ovulation, menstruation or fertilizable condition. A decision as to whether or not they are suffering PMS cannot be made from the record of basal body temperature. Nowadays women have been increasingly interested in the adverse effect on their daily lives caused by PMS, which are likely to start seven days earlier than the start of menstruation. Some examples of such adverse effect are: headache, restlessness, abdominal pain, edema or other unpleasing condition. As a psychological treatment for PMS their realizing that they are put in condition of "PMS" can reduce effectively their sufferings.

One object of the present invention is to provide a method of making a decision on the monthly physiological condition of a female body, including PMS, thus facilitating a woman's daily healthcare as well as birth control. Another object of the present invention is to provide an apparatus which makes a decision on the monthly physiological condition of a female body. Still another object is to provide an apparatus which produces some useful data in making such a decision.
Means for Solving the Problem:

According to one aspect of the present invention, a method of making a decision on the monthly physiological condition of a female body comprises the steps of: determining the bioelectric impedance of the female body periodically to provide a historical record of bioelectric impedance representing how it has been varying; and making a required decision by comparing the present bioelectric impedance with the historical record of bioelectric impedance.

According to another aspect of the present invention, a method of making a decision on the monthly physiological condition of a female body comprises the steps of: determining the bioelectric impedance and the weight of the female body periodically; making a modification of each bioelectric impedance in terms of the weight to provide a historical record of weight-modified bioelectric impedance representing how it has been varying; and making a required decision by comparing the present weight-modified bioelectric impedance with the historical record of weight-modified bioelectric impedance.

The bioelectric impedance of the female body may be determined every day.

The bioelectric impedance of the female body may be determined when she wakes up every day.

The bioelectric impedance appearing between two points selected on both feet may be determined.

According to still another aspect of the present invention, an apparatus which produces some data for making a decision on the monthly physiological condition of a female body comprises: a bioelectric impedance meter; a bioelectric impedance memory which stores a historical record of bioelectric impedance; and a display which has a function of showing the historical record of bioelectric impedance, representing how it has been varying.

The apparatus may further comprise a weight meter, said display having another function of showing the present weight of the female body.

According to still another aspect of the present invention, an apparatus which produces some data for making a decision on the monthly physiological condition of a female body comprises: a bioelectric impedance meter; a weight meter, a processor which makes a modification of each bioelectric impedance in terms of the weight; a weight-modified bioelectric impedance memory which stores a historical record of weight-modified bioelectric impedance, and a display having a function of showing the historical record of weight-modified bioelectric impedance, representing how it has been varying.

Said display may have another function of showing the present weight of the female body.

The apparatus may further comprise a temperature meter and a temperature memory which stores a historical record of temperature, said display having another function of showing the historical record of temperature, representing how it has been varying.

The apparatus may further comprise an arithmetic unit which determines the body fat percentage in terms of the bioelectric impedance, said display having another function of showing the body fat percentage thus determined.

According to still another aspect of the present invention, an apparatus which makes a decision on the monthly physiological condition of a female body comprises: a bioelectric impedance meter; a bioelectric impedance memory which stores a historical record of bioelectric impedance; a decision making unit which makes a required decision by comparing the present bioelectric impedance with the historical record of bioelectric impedance; and a display which has a function of showing the result of the decision thus made.

The apparatus may further comprise a weight meter, said display having another function of showing the present weight of the female body.

The apparatus may further comprise a temperature meter and a temperature memory which stores a historical record of temperature, thus permitting said decision making unit to make a required decision by comparing the present temperature with the historical record of temperature in addition to the comparison of the present bioelectric impedance with the historical record of bioelectric impedance.

According to still another aspect of the present invention, an apparatus which makes a decision on the monthly physiological condition of a female body comprises: a bioelectric impedance meter; a weight meter; a processor which makes a modification of each bioelectric impedance in terms of the weight; a weight-modified bioelectric impedance memory which stores a historical record of weight-modified bioelectric impedance; a decision making unit which makes a required decision by comparing the present weight-modified bioelectric impedance with the historical record of weight-modified bioelectric impedance; and a display which has a function of showing the result of the decision thus made.

Said display may have another function of showing the present weight of the female body.

The apparatus may further comprise a temperature meter and a temperature memory which stores a historical record of temperature, thus permitting said decision making unit to make a required decision by comparing the present temperature with the historical record of temperature in addition to the comparison of the present weight-modified bioelectric impedance with the historical record of weight-modified bioelectric impedance.

Said monthly physiological condition of the female body may pertain to the PMS.

The apparatus may further comprise an input device which inputs extra data pertaining to the menstrual period, thus permitting said decision making unit to take such extra data into account.

Said extra data may include the starting date of the menstrual period and/or the ending date of the menstrual period.

Said display may have another function of showing an advisory message pertaining to the decision on the monthly physiological condition.

Said advisory message may include advise pertaining to the manner of living, including dieting.

The apparatus may further comprise an arithmetic unit which determines a body fat percentage in terms of the bioelectric impedance, said display having another function of showing the body fat percentage thus determined.

BRIEF DESCRIPTION OF THE DRAWINGS

Other objects and advantages of the present invention will be understood from the following description of some preferred embodiments, which are shown in accompanying drawings.

DETAILED DESCRIPTION OF THE INVENTION

Before entering the description of the present invention the relation between the monthly physiological condition of a female body and the bioelectric impedance (hereinafter referred to as "BI") of the female body is described.

After making similar tests repeatedly on a plurality of subjects or female bodies, the inventor found that the BI is correlated closely with the monthly physiological condition, and he had the idea of using the correlation therebetween in making a decision on the monthly physiological condition of a female body. Some accompanying drawings (FIGS. 1 to 8) show examples of measurements, which were conducted on a selected subject when waking up every morning. As for the BI of the subject it appeared between two selected points on the subject's both feet.

Figure 2:
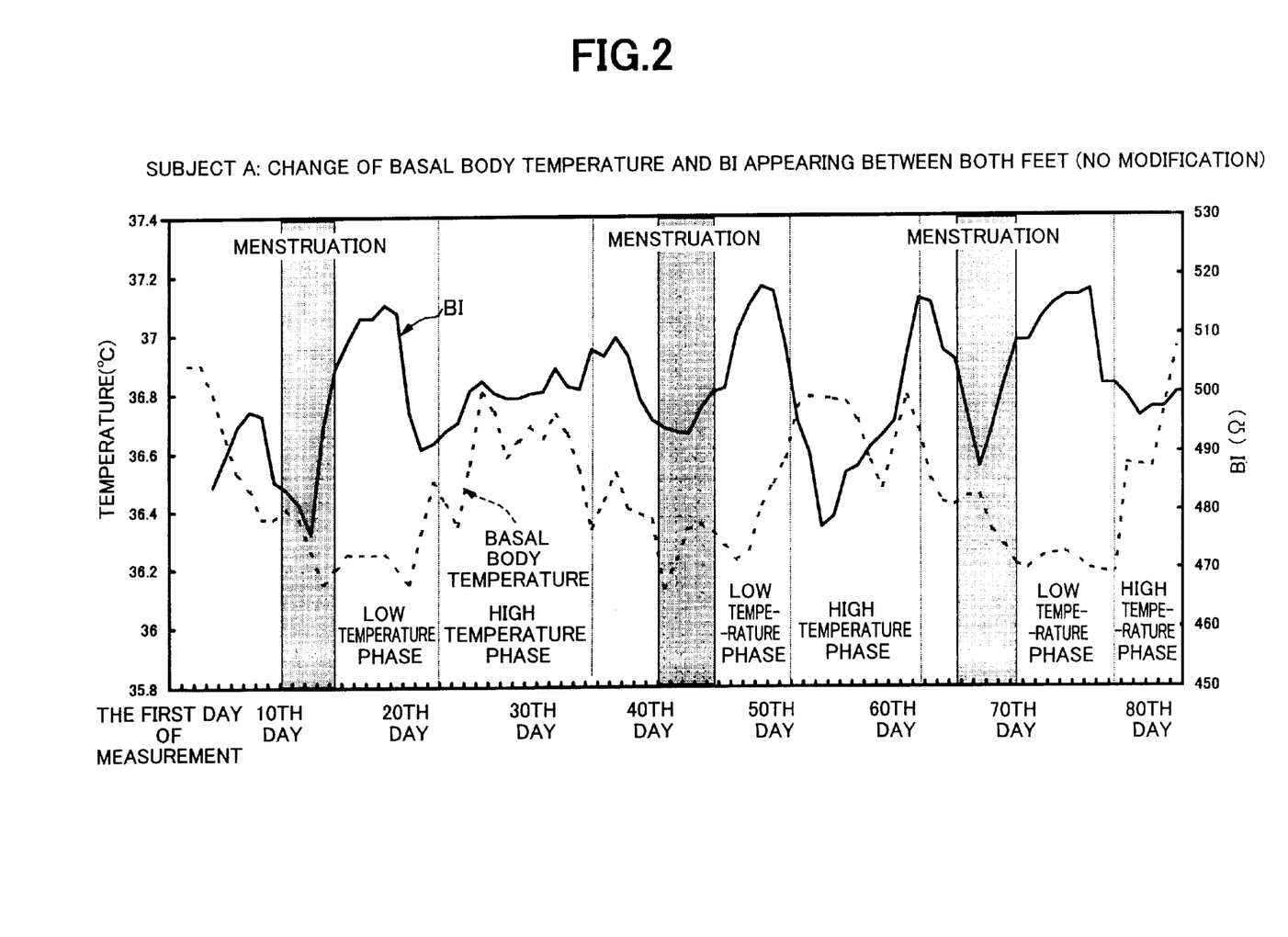
FIG. 2 illustrates how the BI and the basal body temperature (ordinate) vary with time (abscissa)

FIG. 2 shows how the BI and the basal body temperature change cyclically. Specifically the curves of the BI and the basal body temperature are given by plotting the averages of every two adjacent measurements according to the method of moving averages. As a general tendency both the BI and the basal body temperature vary cyclically, the correlation between these respective cyclical variations being as follows: the basal body temperature remains at low values (called "low temperature phase") while the BI remains at high values, the BI remains at low values while the basal body temperature remains at high values (called "high temperature phase"), and the sudden rise and fall of the BI appear for the relatively short length of time beginning with the start of premenstruum and ending with the end of the first half of the following menstrual period.

Figure 3:
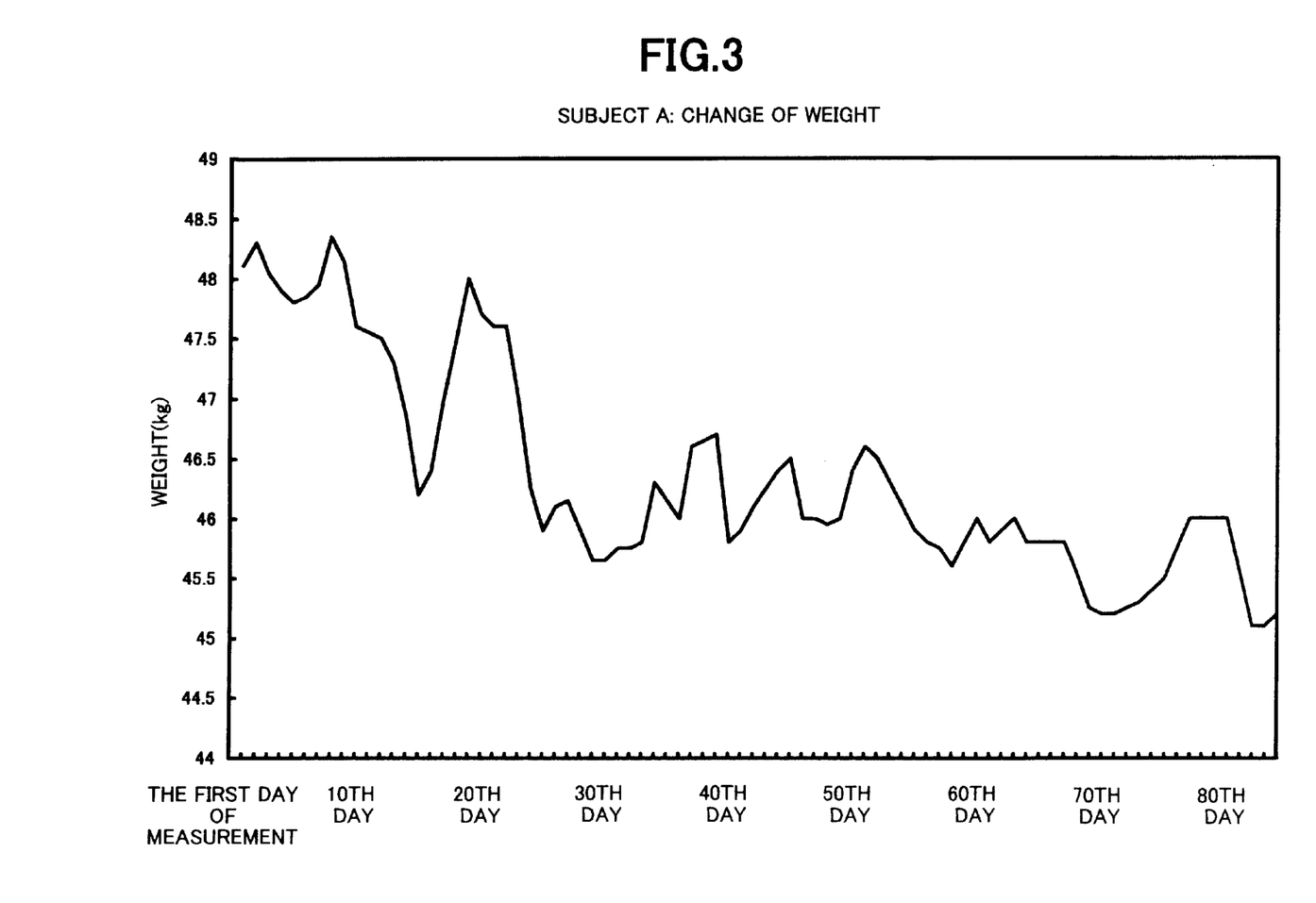
FIG. 3 shows how the weight (ordinate) varies with time (abscissa)
Figure 4:
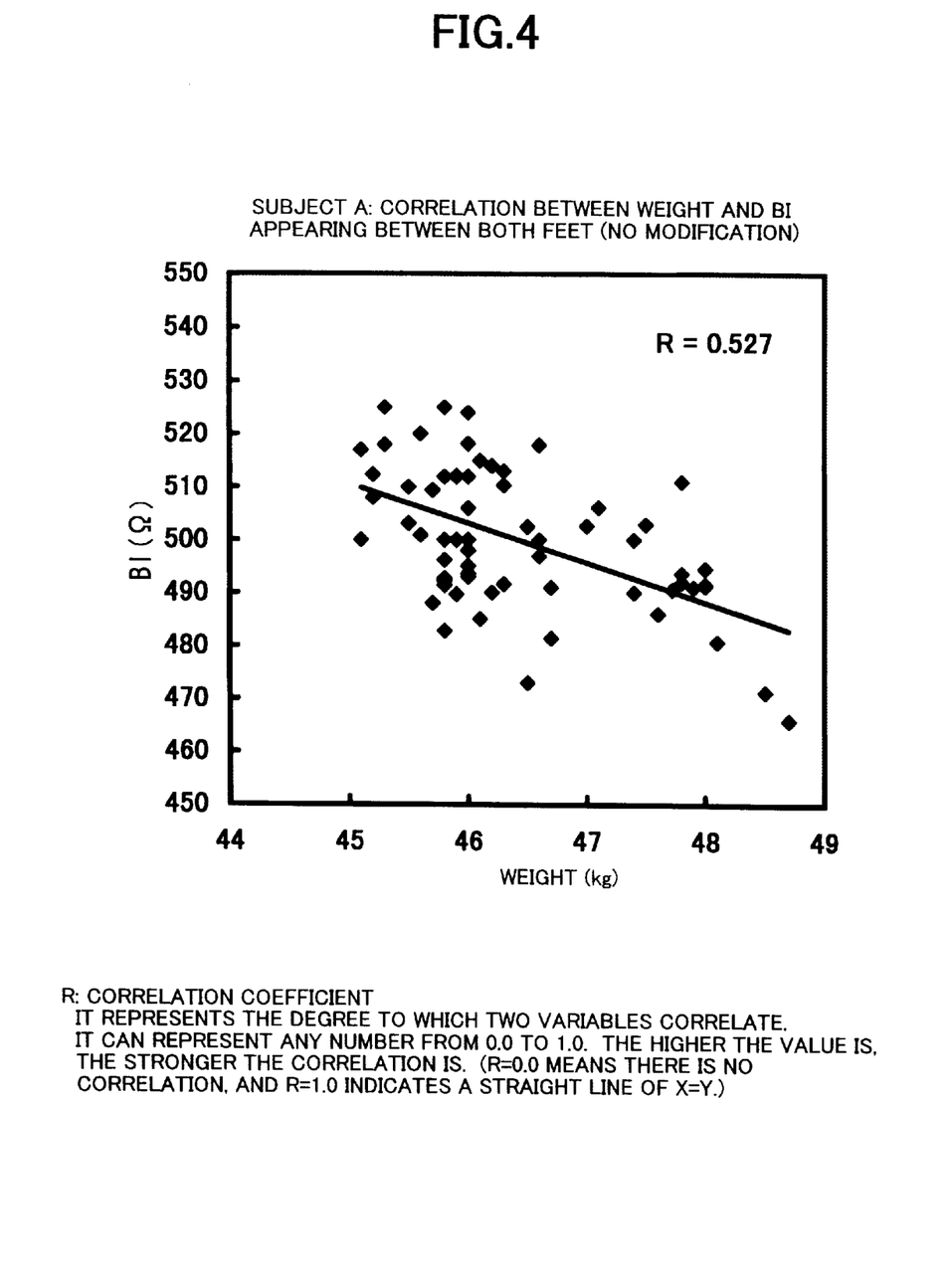
FIG. 4 shows how the BI (ordinate) is correlated with the weight (abscissa)

Now, the correlation between the weight and the BI of the selected subject is described by referring to data shown FIGS. 3 and 4. While the measurement was conducted on the selected subject the weight continued to change gradually with time, as seen from FIG. 3. FIG. 4 shows how the BI is correlated with the weight. It can be seen that there is a significant negative correlation between the BI and the weight (the correlation coefficient "R" being equal to 0.527).

Specifically the BI increases as the weight decreases, or the BI reduces as the weight increases. Such correlation may be justly considered to come from the findings or confirmed facts of: first, the water content of the body increasing in proportion to the increase of the weight; and second, the BI decreasing in proportion to the increase of the water content of the body. From this recognition it is concluded that the BI graph of FIG. 2 be affected more or less by the continuous change of the weight as seen from FIG. 3. To provide a correct graphic representation, therefore, it is necessary to modify the BI graph of FIG. 2 with the weight.

Figure 5:
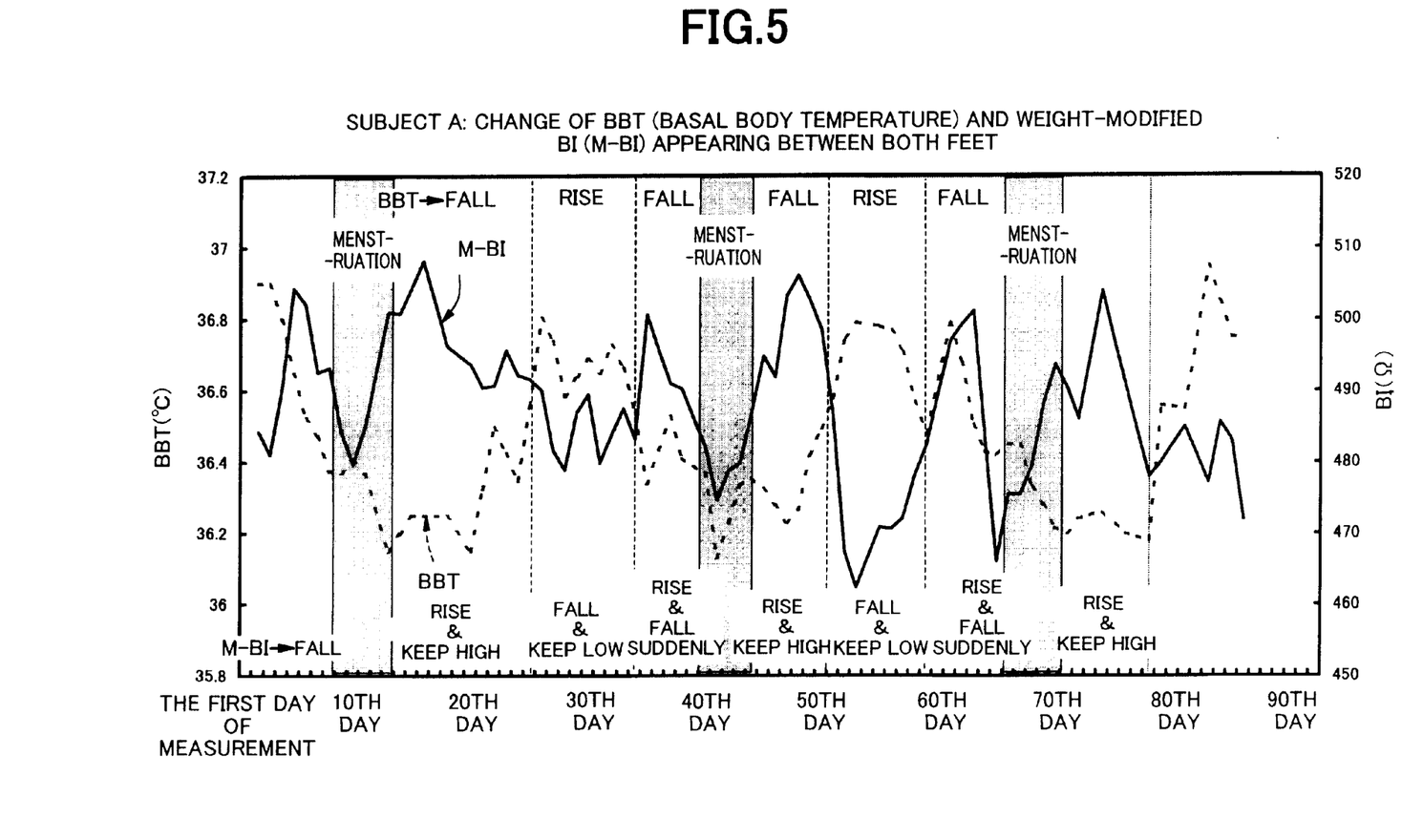
FIG. 5 shows how the weight-modified BI and the basal body temperature (ordinate) vary with time (abscissa)
Figure 6:
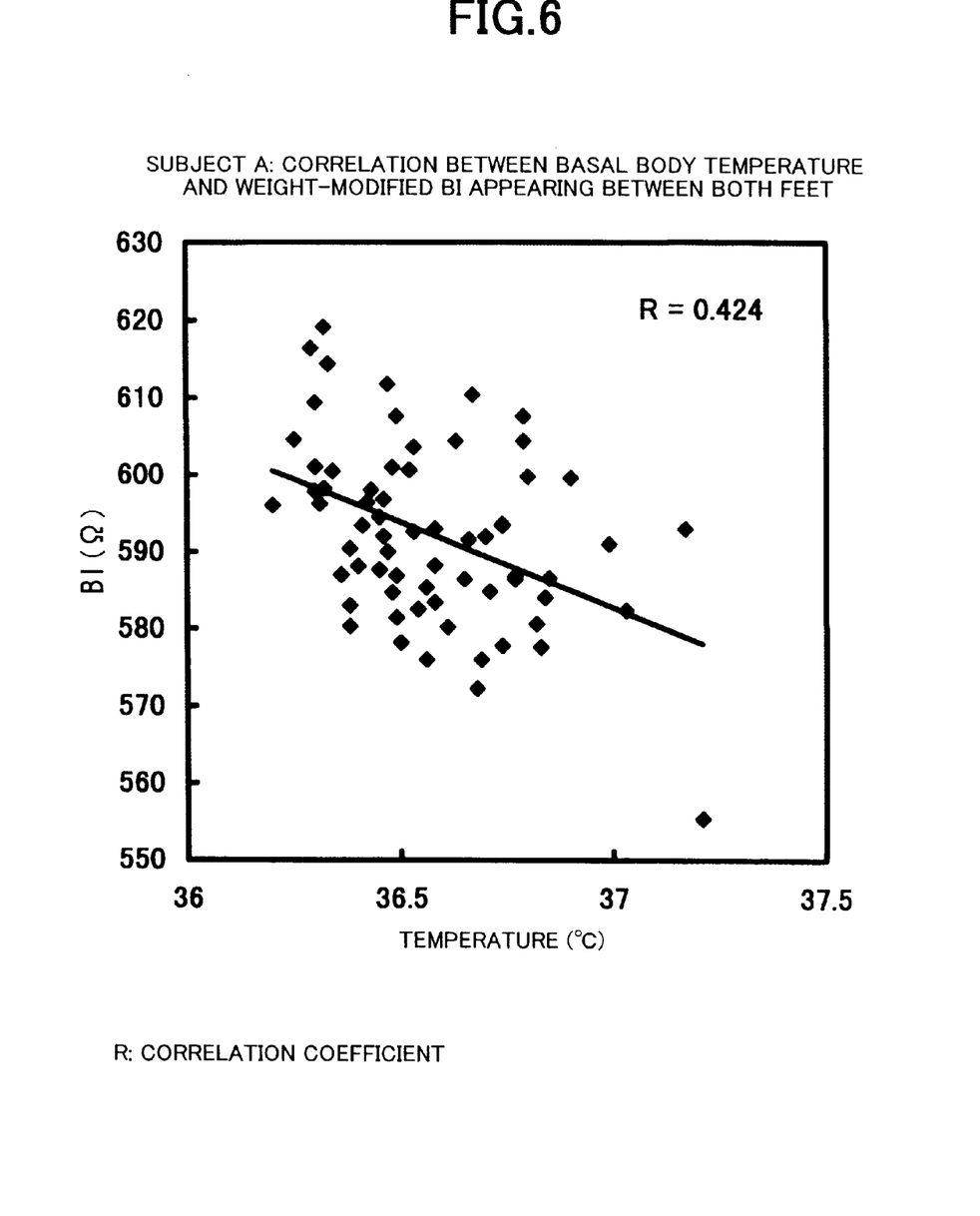
FIG. 6 shows how the weight-modified BI (ordinate) is correlated with the basal body temperature(abscissa)

FIG. 5 is a graph of FIG. 2 modified with weight, showing that the weight-modified BI and the basal body temperature change cyclically. The measured BI can be modified with the weight by adding to the measured BI the decrement of BI which is proportional inversely to the increment of weight or by subtracting from the measured BI the increment of the BI which is proportional inversely to the decrement of the weight, thus eliminating the influence on the graphic representation by the continuous change of the weight. Such weight-modified BI can be calculated from the following equation 1 or 2:

weight-modified BI=BI+A×difference of weight from the first weight (1) or weight-modified BI=BI+B×difference of weight from the preceding weight (2), where A and B stand for modification coefficients. Comparison with FIG. 2 reveals that the graphic representation of FIG. 5 is conspicuous by its cyclic change of the BI, which curve is now free of the influence by the weight change.

Next, the manner in which the BI, the basal body temperature and the PMS are correlated is described. As seen from FIGS. 2 and 5, in general, the BI exhibits high values during the low temperature phase, and exhibits low values during the high temperature phase. As a noticeable change, the BI exhibits low values for the extra period beginning with the start of the premenstruum and ending with the end of the first half of the following menstrual period. The extra period is a substantial part of the low temperature phase of the basal body temperature. In the low temperature phase there appear two peaks and the intervening valley point in the BI curve, implying that the basal body temperature is not substantially correlated with the BI. The least correlation between the basal body temperature and the BI can be confirmed from FIG. 6 (correlation coefficient R=0.424).

Low values of the BI appearing for the extra period of the low temperature phase may be justly attributable to the fact that the female body contains as much water as the edema appears, the edema is getting worse as the water content increases, and accordingly the BI decreases. Thus, the BI appears to be closely related with the edema: the BI exhibits low values when the edema appears, and the BI exhibits high values when the edema disappears. Observation of the BI over an elongated term permits the making of a decision on the subject suffering from the edema. Such decision has been hitherto impossible so far as the measurement of the basal body temperature is used. Also, it is well known that the edema appearing in the premenstruum has a close connection with PMS: the edema is getting worse, and the PMS is getting worse in unison. This suggests that a decision on the suffering from PMS be made on the basis of the continuous change of the BI.

Figure 7:
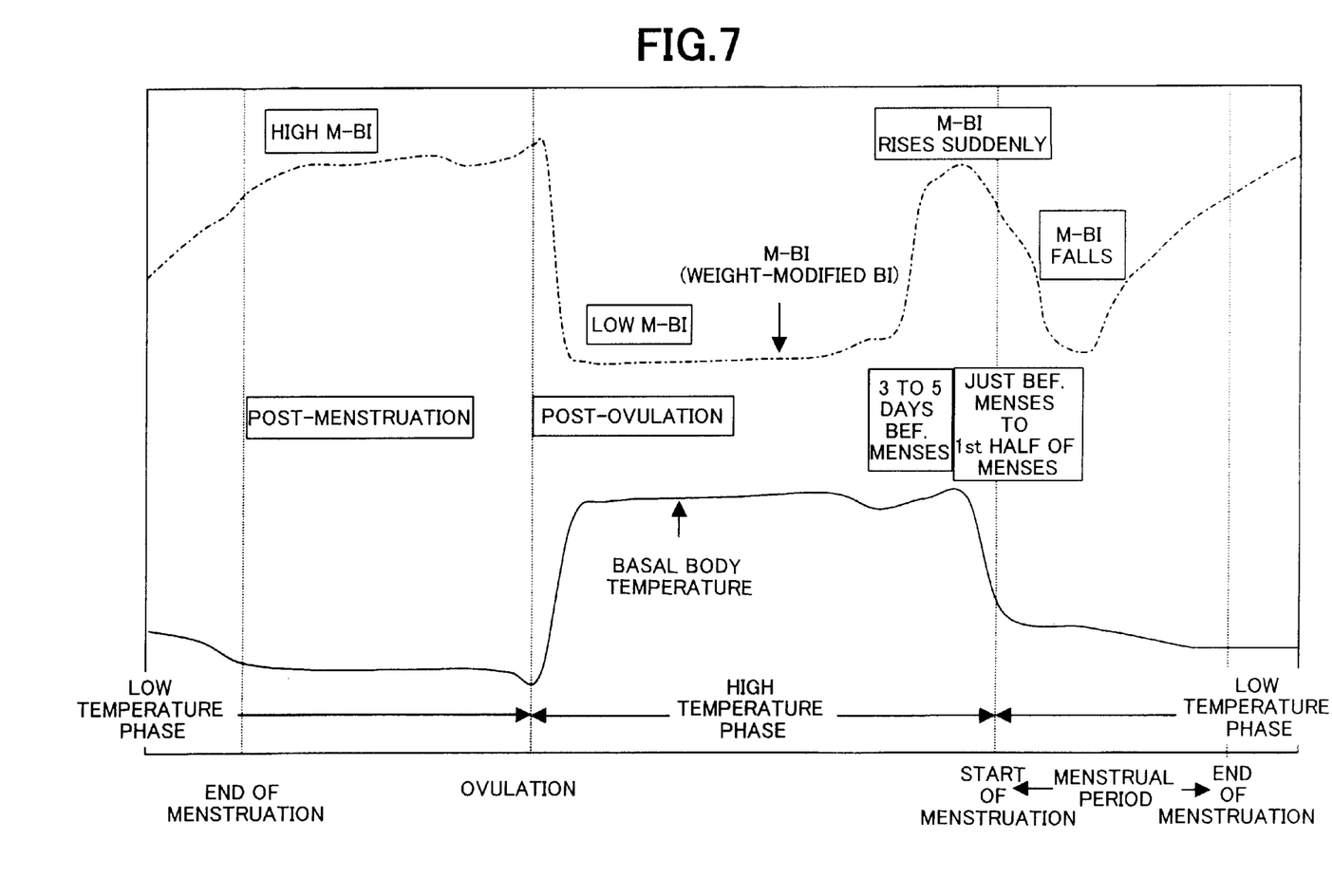
FIG. 7 illustrates how the weight-modified BI, the basal body temperature (ordinate) and the monthly physiological condition of a female body vary with time (abscissa)
Figure 8:
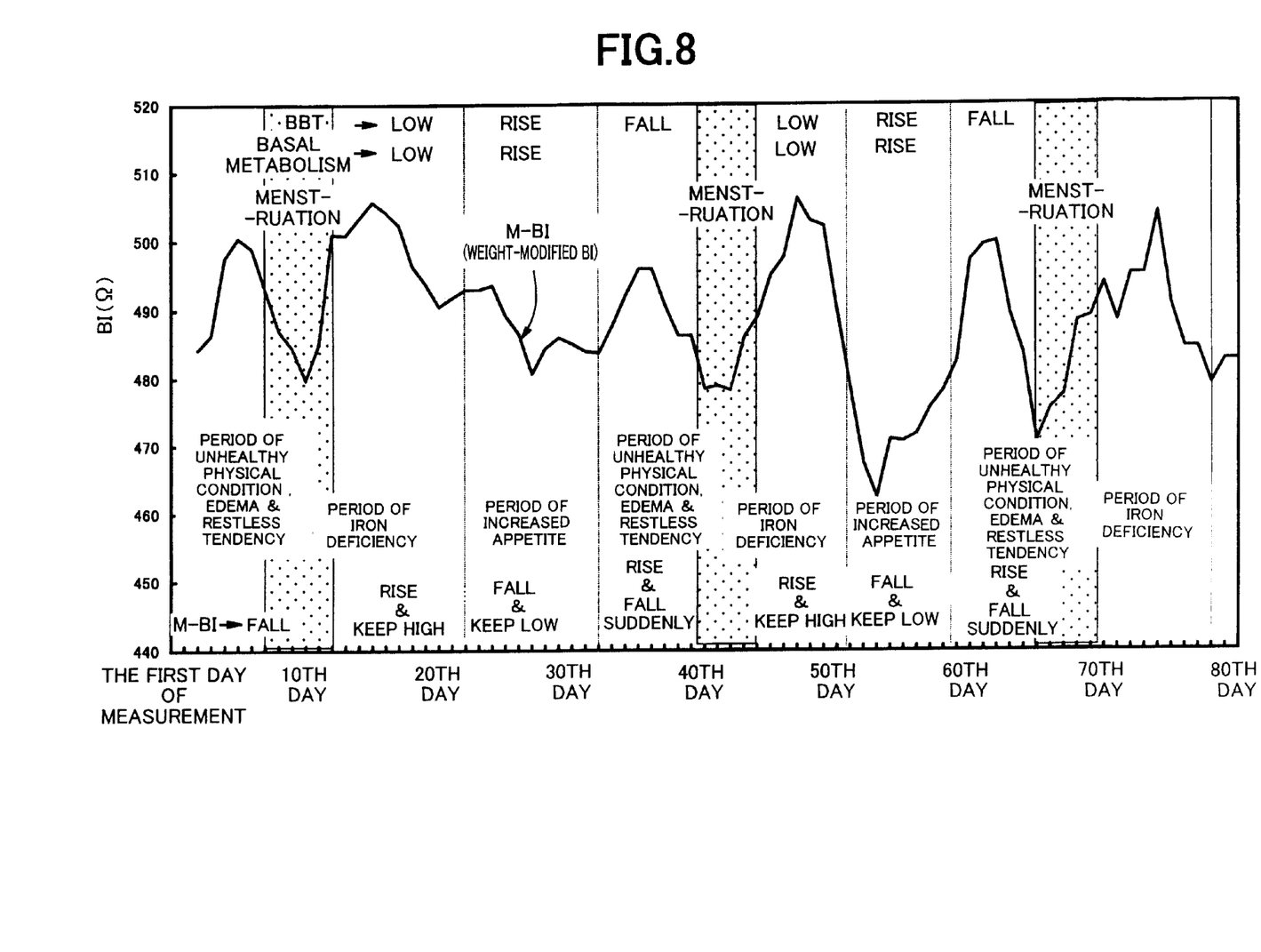
FIG. 8 illustrates how the weight-modified BI (ordinate), the basal body temperature and the monthly physiological condition of a female body vary with time (abscissa)

Next, reference is made to FIGS. 7 and 8, describing the relation between the weight-modified BI (or the BI) and the monthly physiological condition of the selected female body. These figures definitely show that the weight-modified BI curve varies cyclically, and that it is so related with the monthly physiological condition of the female body that a decision on the monthly physiological condition of the female body may be made on the basis of the continuous change of the weight-modified BI curve. Specifically the high-to-low value transition of weight-modified BI appearing at the boundary between the low temperature phase and the high temperature phase indicates that the ovulation has occurred. The high-to-low value transition of weight-modified BI is followed by the level off-and-sudden rise of the weight-modified BI. The sudden rise shows entrance into the premenstruum, indicating that the edema and the PMS appear soon. The sudden rise is followed by the sudden fall, which indicates the start of menstruation. The sudden fall is followed by the gradual rise-and-level off. The gradual rise indicates the end of PMS, and the beginning of the level-off indicates the end of menstruation.

The same inclination as described above with respect to one selected subject was observed in each of the other subjects, and may be presumably observed in women in general. In the experiments the BI appearing between two selected points on both feet of each subject was measured. Other BIs measured between two points selected on a female body can be used equally, but the BI appearing between two selected points on both feet shows a clearly discernible cyclic change compared with other BIs, thus facilitating the making of a decision on physiological condition of a female body.

Now, an apparatus which makes a decision on the monthly physiological condition of a female body according to a first embodiment of the present invention is described.

Figure 9:
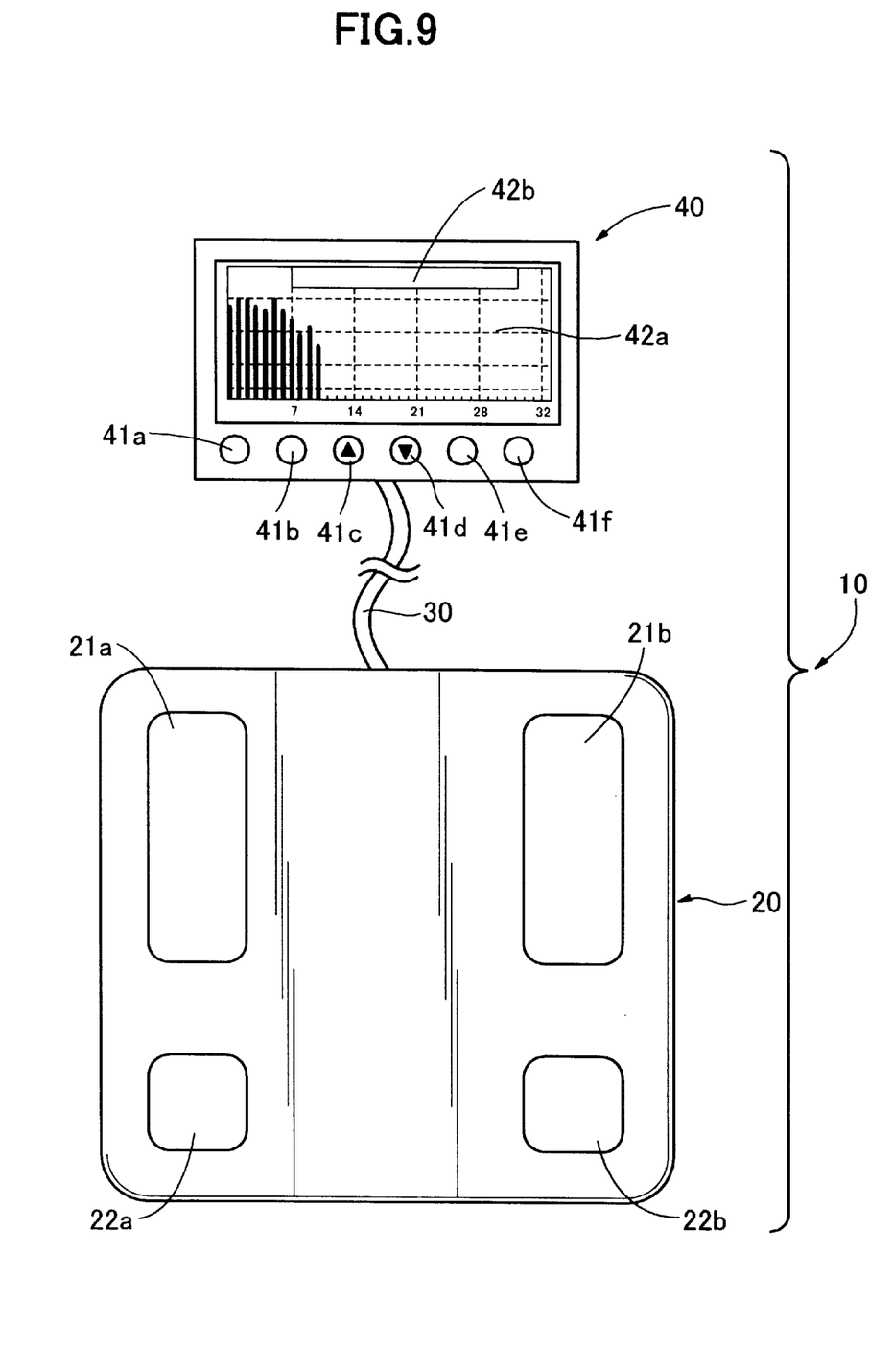
FIG. 9 is a frontal view of an apparatus which makes a decision on the monthly physiological condition of a female body according to a first embodiment of the present invention.

Referring to FIG. 9 the decision making apparatus comprises a weighing scale type of bioelectric impedance meter 20, and a control box 40 connected to the bioelectric impedance meter 20 via a cable 30. Instead of the cable 30, wireless communication such as infrared communication may be used.

The bioelectric impedance meter 20 has a pair of constant-current applying electrodes 21a and 21b and a pair of voltage measuring electrodes 22a and 22b applied to its top surface. The control box 40 has a display screen 42a on its front. The display screen 42a includes an advisory message display area 42b. On the front of the control box 40 there appear a set of operation keys, including an power switch 41a, a measurement-start-command inputting key 41b, a scroll-up key 41c, a scroll-down key 41d, a menstruation-start-day inputting key 41e, and a menstruation-end-day inputting key 41f.

Figure 10:
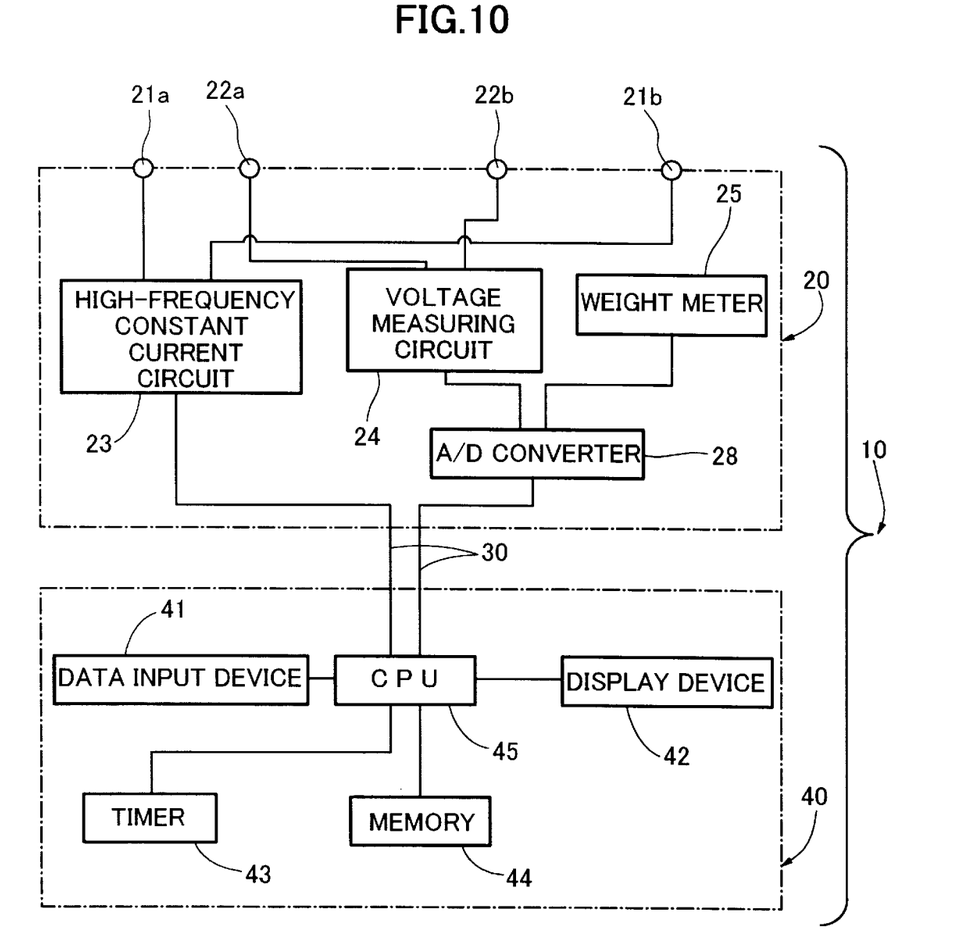
FIG. 10 illustrates the arrangement of major elements of the decision making apparatus of FIG. 9.

FIG. 10 illustrates the arrangement of major elements of the decision making apparatus of FIG. 9. As shown, the bioelectric impedance meter 20 comprises: a high-frequency constant current circuit 23 which supplies the pair of constant current applying electrodes 21a and 21b with a weak constant current; a voltage measuring circuit 24 which measures the voltage between the opposite voltage measuring electrodes 22a and 22b; a weight meter which measures the weight of a subject 25; and an A/D converter 28 which converts analog voltage-and weight-representative signals in digital form.

The control box 40 comprises a data input device 41 including the operation keys 41a to 41f as described above, a display device 42, a timer 43, a memory 44 and a CPU 45. The display device 42 is capable of showing the measured BI curve, the determined monthly physiological condition, and so forth on its display screen 42a. The timer 43 is used in determining at what time or day the measurement is conducted. The memory 44 stores the measured BIs, the time and date on which a required measurement is made, and so forth. Finally, the CPU 45 makes a decision on the monthly physiological condition of a female body on the basis of the menstrual period data inputted at Steps 10 to 14 (later described), the measured BIs, the weights and other data. Also, the CPU controls the memory 44, the display device 42 and other components in the coordinated way.

Some selected components may be changed in position, as for instance the CPU 45 is shifted to the bioelectric impedance meter 20. The weighing scale type of bioelectric impedance meter 20 may be so designed as to incorporate the control box 40, as in a decision making apparatus according to a second embodiment (later described).

Next, a method of making a decision on the monthly physiological condition according to the present invention is described below by referring to the manner in which the decision making apparatus just described works accordingly.

Figure 11:
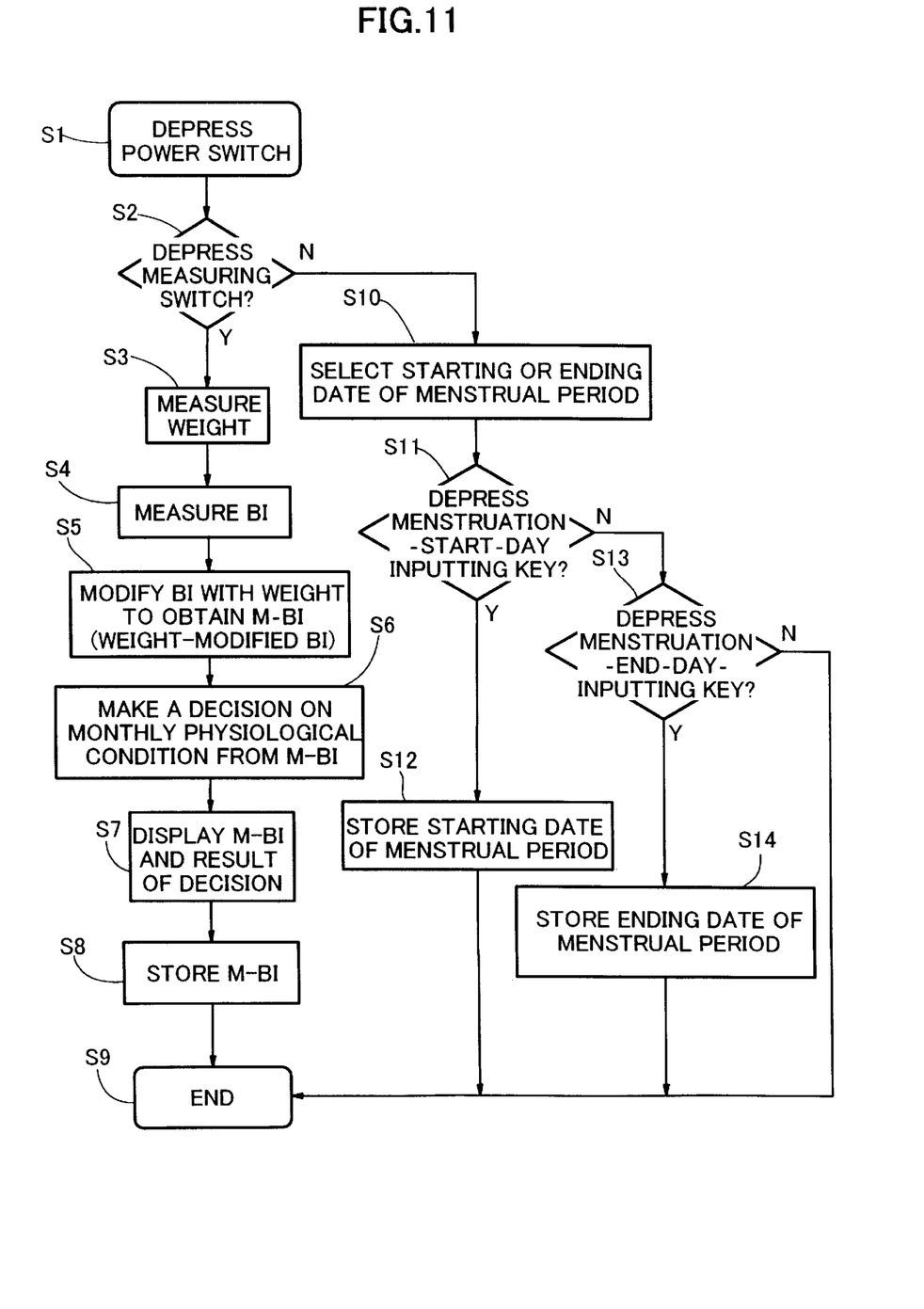
FIG. 11 is a flowchart illustrating a series of actions for making a decision on the monthly physiological condition of a female body.

FIG. 11 is a flowchart illustrating a series of actions for making a required decision. At Step 1 a subject depresses the power switch 41a to turn the decision making apparatus 10 on. At Step 2 depression of the measuring switch 41b allows the proceeding to go to Step 3, in which the decision making apparatus is put in the measuring mode. The measuring switch 41b being not depressed, the proceeding is allowed to go to Step 10 in which the decision making apparatus is put in the data-presetting mode in which the menstrual length of time is inputted and recorded for the use of decision making.

At Step 3 the decision making apparatus starts working in the measuring mode. The subject stands on the bioelectric impedance meter 20, the toes and balls of both feet being laid on the opposite constant-current applying electrodes 21a and 21b, and the heels of both feet being laid on the opposite voltage measuring electrodes 22a and 22b. The weight meter 25 is responsive to the weight for measuring it automatically. At Step 4 a weak constant current is directed from the high-frequency constant current circuit 23 to both toes and balls via the opposite constant-current applying electrodes 21a and 21b, thus allowing the constant current to flow between both legs through the abdominal region. Then, the voltage appearing between the opposite voltage measuring electrodes 22a and 22b is determined, and the BI is calculated from the so determined voltage and the current flowing in the abdominal part of the subject. At Step 5 the BI thus obtained is modified according to either equation as described above, thereby normalizing the BI with respect to a given reference value of weight. Thus, the weight-modified BI is free of the influence by the present weight change.

At Step 6 a decision as to which monthly physiological condition of the female body the subject has been in, as for instances, she has been in ovulatory condition or has been suffering from PMS, is made from the present weight-modified BI (as measured at Step 5) and from the record both of the previous weight-modified BI and the menstrual lengths of time (retrieved from the memory 44) in the light of the correlation between the weight modified BI curve and the monthly physiological condition of a female body. At Step 7 the weight modified BI curve and other data appear in the display screen 42a. Specifically, the so made decision and the advisory message pertaining thereto appear on the advisory display area 42b. Some examples of the decisions appearing in the display are: physical conditions such as ovulation, PMS, menstruation, fertilizable condition, and edema, and accompanying mental conditions such as a feeling of unhealthy condition or of restlessness. As one example of the advisory message the manner of living, including dieting is advised as for instance follows:

"you are involved in premenstruum, so that you may suffer from PMS and edema. Calm yourself lest you should be impatient. Take Vitamin BI rich foods";

"You are in menstrual period. You will get rid of the unpleasant condition soon. Take enough iron lest you should be anemia.";

"Menstrual period has finished, and you are now in the best physical condition. You had better take good exercise."; or "You are involved in the ovulatory period, and you are pleasing less and less. Don't overeat yourself."

At Step 8 the weight-modified BI, the weight and so on, which are measured this time, are stored in the memory 44.

Subsequently at Step 9 the decision making apparatus 10 turns off automatically, thus finishing the series of measurements.

As described above, if the measuring switch 41b is not depressed at Step 2, the proceeding is allowed to go to Step 10, in which the decision making apparatus is put in the data-presetting mode in which the menstrual length of time is inputted and recorded for use of decision making.

At Step 10 the starting or ending date of the menstrual period is selected by depressing the scroll-up key 41c or the scroll-down key 41d. Assume that the starting date of the menstrual period is selected, and then, at Step 11 the menstruation-start-day inputting key 41e is depressed to allow the proceeding to go to Step 12, where the starting date of the menstrual period selected at Step 10 is stored in the memory 44.

Assume that the ending date of the menstrual period is selected at Step 10, and then, at Step 11 the menstruation-start-day inputting key 41e is not depressed to allow the proceeding to go to Step 13. There, the menstruation-end-day key 41f is depressed to allow the proceeding to go to Step 14, permitting the ending date of the menstrual period to be stored in the memory 44.

Subsequent to the action taken at Step 12 or 14 or in the negative outcome at Step 13 the proceeding goes to Step 9 wherein the decision making apparatus 10 turns off automatically, terminating the inputting of data.

Figure 12:
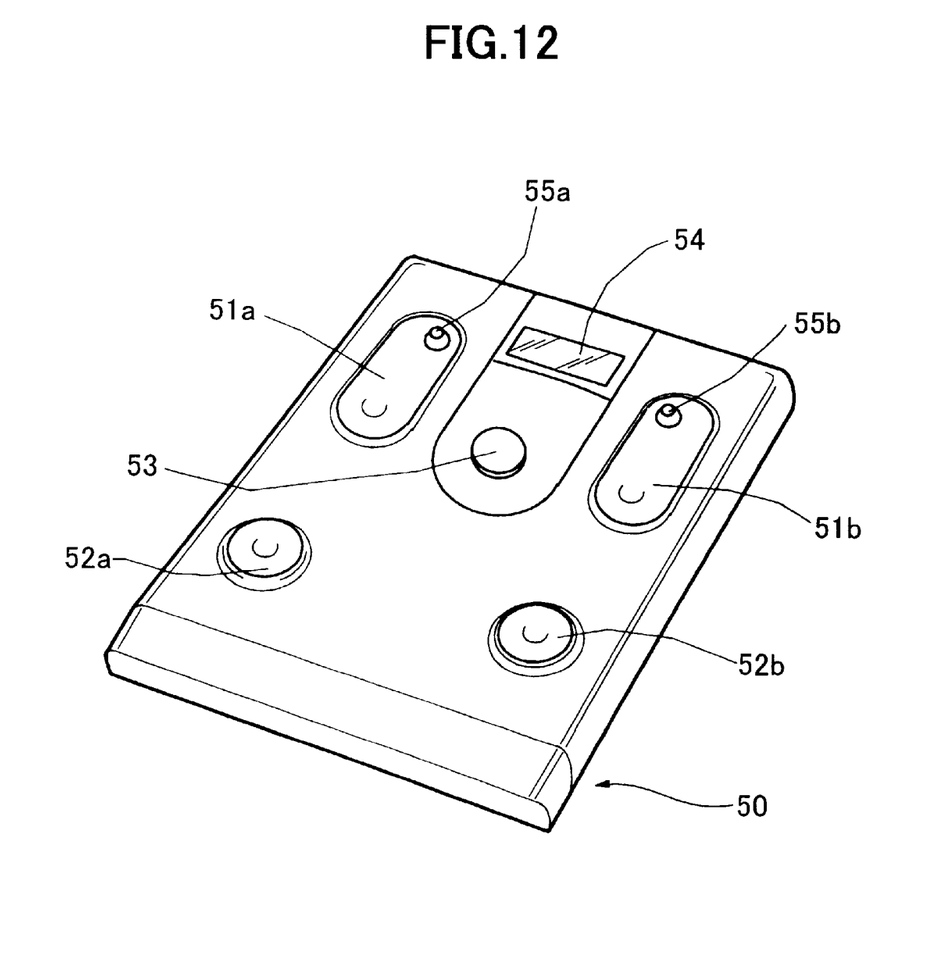
FIG. 12 is a perspective view of a decision making apparatus according to a second embodiment of the present invention.

Next, a decision making apparatus according to a second embodiment of the present invention is described. Referring to FIG. 12, the decision making apparatus 50 is different from the decision making apparatus 10 of FIG. 9 in that: the decision making apparatus 50 has its control box built therein, such a control box 40 being physically separated from the weighing scale type apparatus 20 in FIG. 9; and the decision making apparatus 50 permits body temperature to be measured. The decision making apparatus 50 has a pair of constant-current applying electrodes 51a and 51b, a pair of voltage measuring electrodes 52a and 52b, an operation button 53, and a display screen 54 arranged on its top surface. Each constant-current applying electrode 51a or 51b has a temperature measuring sensor 55a or 55b on its front side. The subject can measure her temperature by pinching each sensor between the large and adjacent toes of each foot. Any other temperature meter which measures the temperature of the subject may be used. For example, a measuring-at-ear type of thermometer may be used by communicating with the decision making apparatus 50 via infrared rays. A sublingual measuring type of gynecological thermometer may be used for measurement of the temperature with precision. When a decision is made on the monthly physiological condition of a female body, relying on the BI along with the so measured temperature, such decision is more reliable than that made with recourse to the BI alone.

While embodiments of the present invention have been described above, the present invention should not be understood as being restricted thereto. The. BI appearing between two selected points on both feet is measured in the above embodiments, but the BI appearing elsewhere may be measured, for example between two selected points on both hands, or either hand and either foot.

The decision making apparatus may be so modified as to permit an access to the memory for retrieving some data pertaining to a selected subject among others, thereby allowing a plurality of subjects to use one and same decision making apparatus in common:

Also, the decision making apparatus may be so modified as to determine the body fat percentage in terms of the measured BI, showing it in the display. Furthermore, the body temperature, the weight and other factors used in making a decision on the monthly physiological condition of a female body may be displayed. This single decision making apparatus thus modified can perform a variety of functions useful for healthcare, including those functions which have been performed hitherto by different conventional apparatuses such as a weighing scale, a thermometer and a body fat meter.

Advantages:

As may be understood from the above, the decision making method and apparatus using the BI as the major factor can make a required decision much quicker and easier than the conventional method and apparatus using the body temperature as the major factor, taking say several seconds to several tens of seconds. Also, there is no worry about falling a sleep unconsciously as would often occur in the conventional way wherein the subject needs to lay in bed without moving only for the sake of measuring one's basal body temperature. In contrast the BI can be measured while the subject is standing. Thanks to use of the BI as the major factor the decision making method and apparatus can be applied to diagnoses of PMS. Thus, the decision making method and apparatus facilitate a woman's daily healthcare as well as birth control, which the application of the conventional method and apparatus has been limited to.

The reliability of the decision making can be improved by adding extra factors of weight and body temperature to the major factor of BI. Still another advantage of the decision making apparatus is that it can be modified to display the body temperature or the weight or to determine the body fat percentage in terms of the measured BI to be able to display this information, whereby this single apparatus alone can perform a variety of functions useful for healthcare, including those functions which have been performed hitherto by different conventional apparatuses such as a weighing scale, a thermometer and a body fat meter.

What is claimed is:

1. A method of making a decision on the monthly physiological condition of a female body, the method comprising the steps of:
    applying pairs of electrodes to selected points of the outer layer of the skin of the female body;
    determining the bioelectric impedance appearing between one of said pairs of electrodes periodically to provide a historical record of bioelectric impedance representing how it has been varying; and
    making the decision by comparing the present bioelectric impedance with the historical record of bioelectric impedance.

2. A method of making a decision on the monthly physiological condition of a female body, the method comprising the steps of:
    determining the bioelectric impedance and the weight of the female body periodically;
    making a modification of each bioelectric impedance in terms of the weight to provide a historical record of weight-modified bioelectric impedance representing how it has been varying; and
    making the decision by comparing the present weight-modified bioelectric impedance with the historical record of weight-modified bioelectric impedance.

3. A method of making a decision on the monthly physiological condition of a female body according to claim 1 wherein the bioelectric impedance of the female body is determined every day.

4. A method of making a decision on the monthly physiological condition of a female body according to claim 1 wherein the bioelectric impedance of the female body is determined when she wakes up every day.

5. A method of making a decision on the monthly physiological condition of a female body according to claim 1 wherein the bioelectric impedance appearing between two points selected on both feet is determined.

6. An apparatus for producing data for making a decision on the monthly physiological condition of a female body, the apparatus comprising:
    a plurality of pairs of electrodes which can be applied to selected points of the outer layer of the skin of the female body;
    a bioelectric impedance meter which measures a bioelectric impedance appearing; between one of said pairs of electrodes:
    a bioelectric impedance memory which stores a historical record of bioelectric impedance; and
    a display for showing the historical record of bioelectric impedance, representing how it has been varying.

7. An apparatus for producing data for making a decision on the monthly physiological condition of a female body according to claim 6 wherein it further comprises a weight meter, said display having another function of showing the present weight of the female body.

8. An apparatus for producing data for making a decision on the monthly physiological condition of a female body, the apparatus comprising:
    a bioelectric impedance meter for measuring a bioelectric impedance of the female body;
    a weight meter for measuring a weight of the female body;
    a processor for modifying the bioelectric impedance based on the weight;
    a weight-modified bioelectric impedance memory which stores a historical record of the weight-modified bioelectric impedance; and
    a display for showing a historical record of weight-modified bioelectric impedance, representing how it has been varying.

9. An apparatus for producing data for making a decision on the monthly physiological condition of a female body according to claim 8 wherein said display has another function of showing the present weight of the female body.

10. An apparatus for producing data for making a decision on the monthly physiological condition of a female body according to claim 6 wherein it further comprises a temperature meter and a temperature memory which stores a historical record of temperature, said display having another function of showing the historical record of temperature, representing how it has been varying.

11. An apparatus for producing data for making a decision on the monthly physiological condition of a female body according to claim 6 wherein it further comprises an arithmetic unit which determines the body fat percentage in terms of the bioelectric impedance, said display having another fiction of showing the body fat percentage thus determined.

12. An apparatus for making a decision on the monthly physiological condition of a female body, the apparatus comprising:
    a plurality of pairs of electrodes which can be applied to selected points of the outer layer of the skin of the female body;
    a bioelectric impedance meter which measures a bioelectric impedance appearing between one of said pairs of electrodes;

a bioelectric impedance memory which stores a historical record of bioelectric impedance;

a decision making unit which makes the decision by comparing the present bioelectric impedance with the historical record of bioelectric impedance; and a display for showing the result of the decision thus made.

13. An apparatus for making a decision on the monthly physiological condition of a female body according to claim 12 wherein it further comprises a weight meter, said display having another function of showing the present weight of the female body.

14. An apparatus for making a decision on the monthly physiological condition of a female body according to claim 12 wherein it further comprises a temperature meter and a temperature memory which stores a historical record of temperature, thus permitting said decision making unit to make the decision by comparing the present temperature with the historical record of temperature in addition to the comparison of the present bioelectric impedance with the historical record of bioelectric impedance.

15. An apparatus for making a decision on the monthly physiological condition of a female body the apparatus comprising:

a bioelectric impedance meter for measuring a bioelectric impedance of the female body;

a weight meter for measuring a weight of the female body;

a processor which makes a modification of the bioelectric impedance based on the weight;

a weight-modified bioelectric impedance memory which stores a historical record of the weight-modified bioelectric impedance;

a decision making unit which makes the decision by comparing the present weight-modified bioelectric impedance with the historical record of weight-modified bioelectric impedance; and a display for showing the result of the decision thus made.

16. An apparatus for making a decision on the monthly physiological condition of a female body according to claim 15 wherein said display has another function of showing the weight of the female body.

17. An apparatus for making a decision on the monthly physiological condition of a female body according to claim 15 wherein it further comprises a temperature meter and a temperature memory which stores a historical record of temperature, thus permitting said decision making unit to make a required decision by comparing the present temperature with the historical record of temperature in addition to the comparison of the present weight-modified bioelectric impedance with the historical record of weight-modified bioelectric impedance.

18. An apparatus for making a decision on the monthly physiological condition of a female body according to claim 12 wherein said monthly physiological condition of the female body is related to PMS.

19. An apparatus for making a decision on the monthly physiological condition of a female body according to claim 12 wherein it further comprises an input device which inputs extra data pertaining to the menstrual period, thus permitting said decision making unit to take such extra data into account.

20. An apparatus for making a decision on the monthly physiological condition of a female body according to claim 19 wherein said extra data includes the starting date of the menstrual period and/or the ending date of the menstrual period.

21. An apparatus for making a decision on the monthly physiological condition of a female body according to claim 12 wherein said display has another function of showing an advisory message pertaining to the decision on the monthly physiological condition.

22. An apparatus for making a decision on the monthly physiological condition of a female body according to claim 21 wherein said advisory message includes advice pertaining to the manner of living, including dieting.

23. An apparatus for making a decision on the monthly physiological condition of a female body according to claim 12 wherein it further comprises an arithmetic unit which determines a body fat percentage in terms of the bioelectric impedance, said display having another function of showing the body fat percentage thus determined.

24. An apparatus for making a decision on the monthly physiological condition of a female body according to claim 15 or 16 wherein said monthly physiological condition of the female body is related to edema.

25. An apparatus for making a decision on the monthly physiological condition of a female body according to claim 15 or 16 wherein said monthly physiological condition of the female body is related to ovulation.

26. An apparatus for making a decision on the monthly physiological condition of a female body according to claim 15 or 16 wherein said monthly physiological conditon of the female body is related to menstruation.

27. An apparatus fpr making a decision on the monthly physiological condition of a female body according to claim 15 or 16 wherein said monthly physiological condition of the female body is related to fertilizable condition.

28. An apparatus for making a decision on the monthly physiological condition of a female body according to claim 21 wherein said advisory message is relating to dieting.

* * * * *